(12) United States Patent
Behler et al.

(10) Patent No.: US 7,585,830 B2
(45) Date of Patent: Sep. 8, 2009

(54) METHOD FOR THE ALKOXYLATION OF ALKYL AND/OR ALKENYL POLYGLYCOSIDES

(75) Inventors: Ansgar Behler, Bottrop (DE); Frank Clasen, Hilden (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 10/598,130

(22) PCT Filed: Feb. 11, 2005

(86) PCT No.: PCT/EP2005/001376

§ 371 (c)(1),
(2), (4) Date: Aug. 18, 2006

(87) PCT Pub. No.: WO2005/087785

PCT Pub. Date: Sep. 22, 2005

(65) Prior Publication Data

US 2007/0161536 A1    Jul. 12, 2007

(30) Foreign Application Priority Data

Feb. 20, 2004   (DE) ................. 10 2004 008 302

(51) Int. Cl.
*C11D 3/22* (2006.01)
*C07H 15/04* (2006.01)
*A61K 8/73* (2006.01)

(52) U.S. Cl. .............. 510/474; 510/121; 510/151; 510/421; 510/470; 510/475; 424/401; 424/488; 424/70.13

(58) Field of Classification Search ................ 510/121, 510/151, 421, 470, 474, 475; 424/401, 488, 424/70.13
See application file for complete search history.

(56) References Cited

U.S. PATENT DOCUMENTS

| | | | |
|---|---|---|---|
| 3,640,998 A | 2/1972 | Mansfield et al. | |
| 3,737,426 A | 6/1973 | Throckmorton et al. | |
| 4,834,903 A * | 5/1989 | Roth et al. ............... | 510/422 |
| 5,958,104 A | 9/1999 | Nonomura et al. | |
| 6,746,988 B2 | 6/2004 | Hopkinson et al. | |
| 2003/0050194 A1 | 3/2003 | Hopkinson et al. | |

FOREIGN PATENT DOCUMENTS

| | | | |
|---|---|---|---|
| DE | 40 40 655 | 6/1992 | |
| EP | 0 364 202 | 4/1990 | |
| WO | WO 86/04899 | * | 8/1986 |
| WO | WO 88/04899 | 8/1988 | |
| WO | WO 99/17608 | 4/1999 | |
| WO | WO 02/085122 | 10/2002 | |
| WO | WO 03/071673 | 9/2003 | |

* cited by examiner

*Primary Examiner*—Brian P Mruk

(57) ABSTRACT

A process for the production of alkoxylated alkyl and/or alkenyl polyglycosides including reacting alkylene oxides with alkyl and alkenyl polyglycosides corresponding to formula (I): $R^1O\text{-}[G]_p$ wherein $R^1$ is an alkyl and/or alkenyl group containing 4-22 carbon atoms, G is a sugar unit containing 5 or 6 carbon atoms and p is a number of 1-10, wherein the alkyl and/or alkenyl polyglycosides corresponding to formula (I) are in the form of a water-containing preparation with a water content of more than 5% by weight, based on the weight of the water-containing preparation is provided. The alkoxylated alkyl and/or alkenyl polyglycosides may be incorporated into agrochemical formulations, herbicides, laundry and dishwashing detergents, cleaning preparations, and pharmaceutical and cosmetic formulations.

2 Claims, No Drawings

METHOD FOR THE ALKOXYLATION OF ALKYL AND/OR ALKENYL POLYGLYCOSIDES

RELATED APPLICATIONS

This application is a national phase filing under 35 U.S.C. § 371 of International Application No. PCT/EP2005/001376 which has an International filing date of Feb. 11, 2005, and which designated the United States of America and which claims priority to German Application No. 102004008302.9, filed Feb. 20, 2004, the entire disclosures of which are hereby incorporated herein by reference.

FIELD OF THE INVENTION

This invention relates generally to nonionic surfactants and, more particularly, to a process for the alkoxylation of alkyl and/or alkenyl polyglycosides and to the use of compounds obtainable by this process as adjuvants in agrochemical formulations or as emulsifiers or surfactants in such preparations as, for example, laundry and dishwashing detergents, domestic cleaners and cosmetic and/or pharmaceutical formulations.

BACKGROUND INFORMATION

The alkoxylation of alkyl groups is a standard chemical reaction in which—depending on the alkylene oxide used—ethylene, propylene and/or butylene oxide adducts of the compounds containing hydroxyl groups are formed. The alkoxylation can even be applied to complex chemical compounds, such as sugar and starch derivatives, providing they contain free hydroxyl groups.

The alkoxylation reactions of complex compounds such as these generally take place at elevated temperatures using a catalyst and in the absence of water.

According to U.S. Pat. No. 3,737,426, the reaction of starch with ethylene glycol is followed by alkoxylation with ethylene oxide and/or propylene oxide in the absence of water at ca. 170° C.

U.S. Pat. No. 3,640,998 recommends carrying out the alkoxylation at 100 to 200° C. using basic catalysts in order to minimize the decomposition of starch. This is a standard alkoxylation reaction in which atmospheric oxygen and water are always removed beforehand.

Finally, reaction mixtures of alkoxylated alkyl mono- and polyglycosides prepared by alkoxylation at 120 to 170° C. using a basic catalyst under substantially water-free conditions are known from U.S. Pat. No. 4,834,903. It is expressly emphasized in this document that the water content of the reaction mixture must be below 5% by weight and preferably below 1% by weight.

The absence of water during the alkoxylation reaction is regarded among experts as absolutely essential because it has hitherto been assumed that the water present in the reaction mixture is responsible for, or influences the amount of, the unwanted secondary product, polyalkylene glycol, formed during the alkoxylation.

However, alkyl polyglycosides are commercially available almost exclusively as water-containing preparations because alkyl polyglycosides and particularly alkyl polyglucosides are highly viscous and barely flowable in water-free form. The commercially available water-containing preparations generally have water contents of at least 10% by weight and, normally, even higher.

If, therefore, alkyl polyglycosides are to be alkoxylated, the water present in commercially available water-containing preparations of the alkyl polyglycosides ought to be removed or reduced to a content of less than 5% by weight before the alkoxylation. However, the removal of water from alkyl polyglycosides is a time-consuming and expensive process which, in addition, is difficult to carry out on a commercial scale on account of the intensive foaming involved in the removal process.

Accordingly, the problem addressed by the present invention was to provide a new process for the alkoxylation of alkyl polyglycosides in which there would be no need to remove water from the alkyl polyglycoside preparations used. At the same time, the reaction product obtained after the process would contain at most small quantities of the unwanted secondary product, polyalkylene glycol.

SUMMARY OF THE INVENTION

Briefly described, according to an aspect of the invention, a process for the production of alkoxylated alkyl and/or alkenyl polyglycosides includes reacting alkylene oxides with alkyl and alkenyl polyglycosides corresponding to formula (I): $R^1O\text{-}[G]_p$ wherein $R^1$ is an alkyl and/or alkenyl group containing 4-22 carbon atoms, G is a sugar unit containing 5 or 6 carbon atoms and p is a number of 1-10, wherein the alkyl and/or alkenyl polyglycosides corresponding to formula (I) are in the form of a water-containing preparation with a water content of more than 5% by weight, based on the weight of the water-containing preparation.

According to other aspects of the invention, the alkoxylated alkyl and/or alkenyl polyglycosides may be incorporated into agrochemical formulations, herbicides, laundry and dishwashing detergents, cleaning preparations, and pharmaceutical and cosmetic formulations.

DETAILED DESCRIPTION OF THE INVENTION

The present invention relates to a process for the production of alkoxylated alkyl and/or alkenyl polyglycosides by reaction of alkylene oxides with alkyl and alkenyl polyglycosides corresponding to formula (I):

$$R^1O\text{-}[G]_p \qquad (I)$$

in which $R^1$ is an alkyl and/or alkenyl group containing 4 to 22 carbon atoms, G is a sugar unit containing 5 or 6 carbon atoms and p is a number of 1 to 10, characterized in that the alkyl and/or alkenyl polyglycosides corresponding to formula (I) are used in the form of water-containing preparations with water contents of more than 5% by weight, based on the water-containing preparation.

Alkyl and/or Alkenyl Polyglycosides

Alkyl and alkenyl polyglycosides are known nonionic surfactants which correspond to formula (I):

$$R^1O\text{-}[G]_p \qquad (I)$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry.

The alkyl and/or alkenyl polyglycosides may be derived from aldoses or ketoses containing 5 or 6 carbon atoms, preferably glucose. Accordingly, the preferred alkyl and/or alkenyl polyglycosides are alkyl and/or alkenyl polyglucosides. The index p in general formula (I) indicates the degree of polymerization (DP), i.e. the distribution of mono- and polyglycosides, and is a number of 1 to 10. Whereas p in a given compound must always be an integer and, above all, may assume a value of 1 to 6, the value p for a certain alkyl polyglycoside is an analytically determined calculated quantity which is generally a broken number. Alkyl and/or alkenyl polyglycosides having an average degree of polymerization p of 1.1 to 3.0 are preferably used. Alkyl and/or alkenyl polyglycosides having a degree of polymerization of less than 1.7 and, more particularly, between 1.2 and 1.4 are preferred from the applicational perspective.

The alkyl or alkenyl group $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl polyglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl polyglucosides based on technical $C_{9/11}$ oxoalcohols (DP=1 to 3) are preferred. In addition, the alkyl or alkenyl group $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl polyglucosides based on hydrogenated $C_{12/14}$ coconut oil fatty alcohol having a DP of 1 to 3 are preferred.

According to the invention, the alkyl and/or alkenyl polyglycosides must be present in the form of water-containing preparations with water contents of more than 5% by weight and must be subjected to the alkoxylation reaction in that form. Alkyl and/or alkenyl polyglycosides corresponding to formula (I) in the form of water-containing preparations with water contents of 10 to 80% by weight and more particularly 30 to 60% by weight, based on the water-containing preparation, are preferably used in the process.

For the actual alkoxylation process, it has proved to be of advantage to introduce the alkyl and/or alkenyl polyglycosides in the form of their water-containing preparations into a stirred pressure reactor, then to add the catalyst and to purge the autoclave thoroughly with nitrogen before the reaction in order to remove all traces of atmospheric oxygen. Thereafter, it is advisable to heat the pressure reactor, the alkoxylation preferably being carried out at temperatures of 80 to 150° C. and more particularly at temperatures in the range from 100 to 120° C. The alkylene oxide, which may be ethylene oxide, propylene oxide, butylene oxide or a mixture thereof, is preferably introduced into the reactor under pressure via a siphon, the autogenous pressure being capable of rising to at most about 5 bar. In a preferred embodiment, an average of 0.5 to 100, preferably 0.5 to 20 and more particularly 1 to 15 mol alkylene oxide, preferably ethylene oxide, is used per mol alkyl and/or alkenyl polyglycoside. The addition of the alkylene oxide takes place statistically, i.e. a complex mixture of alkyl and/or alkenyl polyglycosides alkoxylated to different degrees is obtained in the alkoxylation reaction. The end of the reaction is indicated by a fall in pressure in the reactor. The reaction time is generally between 30 minutes and 2 hours. For safety reasons, it is advisable to leave the mixture to after-react, preferably at the temperatures mentioned above, and then for another 30 minutes at lower temperatures of up to about 80° C. before the reactor is cooled and vented.

The alkoxylation is carried out in the presence of catalysts, preferably basic (alkaline) catalysts, such as sodium methanolate, sodium hydroxide and/or potassium hydroxide. Particularly preferred catalysts are sodium hydroxide and potassium hydroxide which are advantageously used in the form of aqueous solutions generally containing 40 to 60% by weight of catalyst. Suitable quantities of catalyst are 0.1 to 5.0% by weight and preferably 0.2 to 0.6% by weight, expressed as solids and based on reaction product obtained.

COMMERCIAL APPLICATIONS

The present invention also relates to the use of alkoxylated alkyl and/or alkenyl polyglycosides as adjuvants in agrochemical formulations, more particularly as potentiating agents for herbicides.

Agrochemical formulations in the context of the present invention are broadly understood to include any compounds which contain active components from the group of fungicides, fertilizers, herbicides, pesticides, insecticides, plant strengthening agents or other active components for use in horticulture. In a particularly preferred embodiment, the alkoxylated alkyl and/or alkenyl polyglycosides are used in herbicide-containing formulations.

According to the invention, the alkoxylated alkyl and/or alkenyl polyglycosides are used as adjuvants, more particularly as potentiating agents. They have been found to be particularly outstanding in enhancing the effect of glyphosate. The alkoxylated alkyl and/or alkenyl polyglycosides and the active components are generally present in the agrochemical formulations in ratios by weight of 1:40 to 3:1 and preferably in ratios by weight of 1:20 to 1:1.

Glyphosate is N-(phosphonomethyl)glycine, $C_3H_8NO_5P$, MW 169.07, melting point 200° C., $LD_{50}$ (rat, oral) 4320 mg/kg (WHO), a nonselective systemic leaf herbicide which is used in the form of its isopropylamine salt for the total and semitotal control of unwanted grasses and weeds, including deep-rooting several-year-old species, among all agricultural crops, in orchards and vineyards. The structure of glyphosate is as follows:

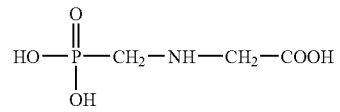

In the context of the present invention, glyphosate is understood to include all the glyphosate derivatives known to the expert, i.e. preferably the mono or diethanolamine salts of glyphosate. Sodium and potassium are also suitable cations. However, the isopropylamine salt of glyphosate is particularly preferred. In addition, mixtures of these compounds may also be used for the purposes of the invention.

The pesticides which may also be present in the agrochemical formulations are preferably oil-soluble substances. Fungicides, herbicides, insecticides or mixtures thereof may be used. Typical examples of suitable fungicides are azoxystrobin, benalaxyl, carbendazim, chlorothalonil, cupfer, cymoxanil, cyproconazol, diphenoconazol, dinocap, epoxyconazol, fluazinam, flusilazol, flutriafol, folpel, fosetyl aluminium, kresoxim methyl, hexaconazol, mancozeb, metalaxyl, metconazol, myclobutanil, ofurace, phentinhydroxide, prochloraz, pyremethanil, soufre, tebucanazol and tetraconazol and mixtures thereof. Suitable herbicides include alachlor, acloniphen, acetochlor, amidosulfuron, aminotriazol, atrazin, bentazon, biphenox, bromoxyl octanoate, bromoxynil, clethodim, chlodinafop-propargyl, chloridazon, chlorsulfuron, chlortoluron, clomazon, cycloxydim, desmedipham, dicamba, dicyclofop-methyl, diurea, diflupheniсаnil, dimithenamid, ethofumesat, fluazifop, fluazifop-p-butyl, fluorochloridon, fluroxypyr, glufosinat, glyphosate, galoxyfop-R, ioxynil octanoate, isoproturon, isoxaben, metamitron, metazachlor, metolachlor, metsulfuron-methyl, nicosulfuron, nofflurazon, oryzalin, oxadiazon, oxyfluorphen, paraquat, pendimethalin, phenmedipham, phenoxyprop-p-ethyl, propaquizafop, prosulfocarb, quizalofop, sulcotrion, sulphosat, terbutylazin, triasulfuron, trichlorpyr, triflualin and triflusulforon-methyl which may be used individually or in admixture with one another. Finally, suitable insecticides include biphenthrin, carbofuran, carbosulfan, chlorpyriphos-methyl, chlorpyriphos-ethyl, β-cyfluthrin, λ-cyhalothrin, cyhexatin, cypermethrin, dicofol, endosulfan, τ-fluvalinat, α-methrin, δ-methrin, phenbutatin, pyrimicarb, terbuphos and tebuphenpyrad and mixtures thereof.

If desired, the agrochemical formulations may contain other typical auxiliaries and additives. Other adjuvants may also be present as optional constituents. For example, nonionic surfactants from at least one of the following groups are suitable for this purpose:

(1) products of the addition of 2 to 120 mol ethylene oxide and/or 0 to 75 mol propylene oxide onto linear fatty alcohols containing 8 to 22 carbon atoms, fatty amines, onto fatty acids containing 8 to 22 carbon atoms, onto alkylphenols containing 8 to 15 carbon atoms in the alkyl group and $C_{6-22}$ fatty amines;
(2) $C_{12,18}$ fatty acid monoesters, diesters and triesters of products of the addition of 1 to 120 mol ethylene oxide onto glycerol and technical oligoglycerols;
(3) glycerol monoesters and diesters and sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) products of the addition of 15 to 60 mol ethylene oxide onto castor oil and/or hydrogenated castor oil;
(6) polyol esters and, in particular, polyglycerol esters such as, for example, polyglycerol polyricinoleate or polyglycerol poly-12-hydroxy-stearate. Mixtures of compounds from several of these classes are also suitable;
(7) products of the addition of 2 to 15 mol ethylene oxide onto castor oil and/or hydrogenated castor oil;
(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(9) trialkyl phosphates and mono-, di- and/or tri-PEG-alkyl phosphates and salts thereof;
(10) wool wax alcohols;
(11) polysiloxane/polyalkyl polyether copolymers and corresponding derivatives;
(12) mixed esters of pentaerythritol, fatty acids, citric acid and fatty alcohol and/or mixed esters of fatty acids containing 6 to 22 carbon atoms, methyl glucose and polyols, preferably glycerol,
(13) polyalkylene glycols and
(14) glycerol carbonate.

The addition products of ethylene oxide and/or propylene oxide onto fatty alcohols, fatty acids, alkylphenols, glycerol monoesters and diesters and sorbitan monoesters and diesters of fatty acids or onto castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic preparations.

It is advisable to use nonpolar solvents, particularly when pesticides that are solid at room temperature are to be incorporated in the emulsions. Suitable nonpolar solvents as a further optional component are, for example, mineral oils, aromatic alkyl compounds and the hydrocarbons marketed, for example, under the name of Solvesso® by Exxon, fatty acid lower alkyl esters such as, for example, the $C_{1-4}$, i.e. the methyl, ethyl, propyl and/or butyl esters of caproic acid, caprylic acid, 2-ethylhexanoic acid, capric acid, lauric acid, isotridecanoic acid; myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Also suitable are vegetable triglycerides such as, for example, coconut oil, palm oil, palm kernel oil, sunflower oil, olive oil and the like. Another suitable solvent is polyethylene glycol, preferably with molecular weights in the range from 90 to 600 and more particularly in the range from 120 to 250.

The agrochemical formulations generally have a water content of on average 10 to 90% by weight and more particularly 30 to 60% by weight. The application solution actually used contains the actual active component in quantities of 0.01 to 5% by weight, preferably in quantities of 0.1 to 2.5% by weight and more particularly in quantities of 0.1 to 1.5% by weight.

However, the agrochemical formulations may also be marketed as concentrates, for example containing 10 to 90% by weight active component, the actual in-use concentration being established by dilution of the concentrate. The water content in such concentrates is between 1 and 30% by weight.

It has been found that the combination of glyphosate with the alkoxylated alkyl and/or alkenyl polyglycosides increases the effect, so that the concentrations of active components used and hence the adverse effects of using such active components on the environment can be effectively reduced.

The present invention also relates to the use of alkoxylated alkyl and/or alkenyl polyglycosides as emulsifiers or surfactants in such preparations as, for example, laundry and dishwashing detergents and/or cleaning preparations or cosmetic and/or pharmaceutical formulations. The alkoxylated alkyl and/or alkenyl polyglycosides are preferably used in cosmetic and/or pharmaceutical formulations, more particularly as potentiating agents for cosmetic active components.

According to the invention, alkoxylated alkyl and/or alkenyl polyglycosides which have been produced by the process according to the invention are preferably used as emulsifiers or surfactants in such preparations as, for example, laundry and dishwashing detergents and/or cleaning preparations or cosmetic and/or pharmaceutical formulations. Again, the alkoxylated alkyl and/or alkenyl polyglycosides are preferably used in cosmetic and/or pharmaceutical formulations.

These preparations may contain as further auxiliaries and additives pearlizing waxes, consistency factors, thickeners, superfatting agents, stabilizers, silicone compounds, fats, waxes, lecithins, phospholipids, antioxidants, deodorants, antiperspirants, antidandruff agents, swelling agents, tyrosine inhibitors, hydrotropes, solubilizers, preservatives, perfume oils, dyes, other surfactants and other typical ingredients encountered, for example, in laundry and dishwashing detergents and cleaning preparations.

Preferred cosmetic and/or pharmaceutical preparations include oral hygiene and dental care preparations, hair shampoos, hair lotions, foam baths, shower baths, creams, gels, lotions, alcoholic and aqueous/alcoholic solutions and emulsions.

The preparations according to the invention may be adjusted to any concentrations by addition of water. Their water content may amount to between 5 and 95% by weight, preferably to between 50 and 90% by weight and more particularly to between 60 and 85% by weight.

The alkoxylated alkyl and/or alkenyl polyglycosides according to the invention may be used in the preparations mentioned in quantities of 0.05 to 40% by weight, preferably in quantities of 0.5 to 25% by weight and more particularly in quantities of 2.5 to 10% by weight, based on the active substance content.

EXAMPLES

Compounds Used

The alkyl polyglucoside commercially available as Plantacare 1200™ from Cognis Deutschland GmbH & Co. KG was used in the following Examples. It is an aqueous preparation containing 51.2% by weight of an alkyl polyglucoside based on a hydrogenated $C_{12/14}$ cocoalcohol with a DP of 1.4.

Abbreviations Used

"EO" stands for "ethylene oxide; "+5 EO" means alkoxylated with "5 mol ethylene oxide".

Example 1:

Plantacare 1200+5 EO 697.0 g (corresponding to 0.8 mol) Plantacare 1200™ were introduced into a 1-liter stirred autoclave together with 4.7 g (corresponding to 0.67% by weight, based on starting compound) of an aqueous 50% by weight potassium hydroxide solution. The autoclave was closed and alternately purged with nitrogen three times. 178.4 g (corresponding to 4.0 mol) ethylene oxide were then introduced in portions at max. 120° C./max. 5 bar pressure. The reaction time was 1 hour. After the ethoxylation, the reaction mixture was left to after-react for 1 hour at 120° C. and then for 30 minutes at 80° C., after which the reactor was evacuated to remove residues of unreacted ethylene oxide.

The product formed had the following quality characteristics: content of unreacted Plantacare 1200™ (in % by weight): 8.1, based on monoglucoside polyethylene glycol content (in % by weight): below 0.1
water content (in % by weight): 34.3.

Example 2:

Plantacare 1200+10 EO 568.0 g (corresponding to 0.69 mol) Plantacare 1200™ were introduced into a 1-liter stirred autoclave together with 4.7 g (corresponding to 0.67% by weight, based on starting compound) of an aqueous 50% by weight potassium hydroxide solution. The autoclave was closed and alternately purged with nitrogen three times. 304.0 g (corresponding to 6.9 mol) ethylene oxide were then introduced in portions at max. 120° C./max. 5 bar pressure. The reaction time was 1 hour and 25 minutes. After the ethoxylation, the reaction mixture was left to after-react for 1 hour at 120° C. and then for 30 minutes at 80° C., after which the reactor was evacuated to remove residues of unreacted ethylene oxide.

The product formed had the following quality characteristics: content of unreacted Plantacare 1200™ (in % by weight): 2.2, based on monoglucoside polyethylene glycol content (in % by weight): below 0.1
water content (in % by weight): 24.7.

What is claimed is:

1. A process for the production of alkoxylated alkyl and/or alkenyl polyglycosides comprising:

reacting at least one alkylene oxide with at least one alkyl and/or alkenyl polyglycoside in the presence of about 10% to about 80% by weight of water, based on the weight of the polyglycoside and water, said polyglycoside corresponding to formula (I):

$$R^1O\text{-}[G]_p \qquad (I)$$

wherein $R^1$ is an alkyl and/or alkenyl group containing 4 to 22 carbon atoms, G is a sugar unit containing 5 or 6 carbon atoms and p is a number of 1 to 10.

2. The process according to claim 1, wherein the reaction occurs in the presence of about 30% to about 60% by weight of water, based on the weight of the polyglycoside and water.

* * * * *